United States Patent [19]

Remold

[11] Patent Number: 4,708,937

[45] Date of Patent: Nov. 24, 1987

[54] PURIFIED MIGRATION INHIBITORY FACTOR ALSO HAVING COLONY STIMULATING FACTOR ACTIVITY

[75] Inventor: Heinz G. Remold, Brookline, Mass.

[73] Assignee: Brigham & Women's Hospital, Boston, Mass.

[21] Appl. No.: 660,861

[22] Filed: Oct. 15, 1984

[51] Int. Cl.[4] .............................................. C12N 9/96
[52] U.S. Cl. ....................................... 435/188; 435/7; 435/68; 530/350; 530/351; 530/387
[58] Field of Search .............................. 435/7, 68, 188; 530/350, 351, 387

[56] References Cited

U.S. PATENT DOCUMENTS 4,438,032  3/1984  Golde et al. .................... 260/112 R

FOREIGN PATENT DOCUMENTS 0100641  2/1984  European Pat. Off. .

OTHER PUBLICATIONS

Weiser, W. Y. et al., "Studies on Human Migration Inhibitory Factor: Characterization of Three Molecular Species," J. Immunol. 126(5): 1958–1962 (1981).

Remold, H. G. et al., "Production of Migration-Inhibitory Factor by a Human T-Lymphoblast Cell Line," Cellular Immunol. 78: 305–313 (1983).

Lusis, A. J. et al., "Translation of mRNA for Human Granulocyte-Macrophage Colony Stimulating Factor," Nature 298: 75–77 (1982).

Nathan, I. et al., "Immune ($\gamma$) Interferon Produced by a Human T-Lymphoblast Cell Line," Nature 292:842–844 (1981).

Jentoff, N. et al., "Labeling of Proteins by Reductive Methylation Using Sodium Cyanoborohydride," J. Biol. Chem. 254(11): 4359–4365 (1979).

Remold, H. G. et al., "Two Migration Inhibitory Factors with Different Chromatographic Behavior and Isoelectric Points," J. Immunol. 118(6): 2015–2019 (1977).

*Primary Examiner*—Christine M. Nucker
*Attorney, Agent, or Firm*—Saidman, Sterne, Kessler & Goldstein

[57] ABSTRACT

Human migration inhibitory factor (MIF) and salts and derivatives thereof, substantially free of impurities.

5 Claims, 4 Drawing Figures

PURIFIED MIGRATION INHIBITORY FACTOR ALSO HAVING COLONY STIMULATING FACTOR ACTIVITY

The present invention was made utilizing funds of the United States Government. The Government has certain rights in this invention.

BACKGROUND OF THE INVENTION

1. Field of the Invention

The invention relates to a substantially purified form of migration inhibitory factor (MIF), a process of preparing the same and uses therefor.

2. Brief Description of the Background Art

Following activation, lymphocytes generally manufacture and secrete soluble substances variously referred to as factors, mediators or lymphokines, that affect the behavior of other cells. The factors can be divided into various groups according to the target cell they affect (macrophage, granulocyte, lymphocyte, or other). The three main effects of factors on macrophages are inhibition of macrophage migration, macrophage activation and macrophage chemotaxis. One of these factors, migration inhibitory factor (MIF), is the subject of the present invention.

MIF was the first mediator discovered. Lymphocytes from normal unimmunized animals do not produce MIF in measurable quantities, apparently because they are not stimulated in sufficient numbers by the antigen. For a similar reason, lymphocytes immune to one antigen will not produce measurable amounts of MIF when exposed in culture to another antigen. Normal lymphocytes, however, will produce MIF when activated by mitogens such as concanavalin A, for these substances activate a fair proportion of the lymphocyte population.

MIF has been demonstrated in most mammals, including humans. Its action is not species specific: for example, MIF of human origin inhibits macrophages obtained from guinea pigs.

In vitro MIF production can be demonstrated 4–6 hours after lymphocyte stimulation, and the stimulated cells continue to produce MIF for as long as four days, provided the stimulus persists. In vivo, the production of MIF—as well as that of most other mediators—is associated with delayed type hypersensitivity (DTH). Generally, the first exposure of a patient or animal to a given microorganism or to a non-bacterial protein produces no noticeable change, but the immune status of the recipient is clearly altered. The sign of this alteration is the fact that the recipient normally reacts differently to a second injection of the same antigen than it does to the first one. The first injection makes the animal hypersensitive to renewed antigen exposure; the major sign of this condition is the development of a characteristic skin lesion at the injection site—a lesion not seen after the first antigen exposure. Since the response to the second antigen inoculum is delayed by 24–48 hours, the reaction is referred to as a DTH. In humans, the sensitizing antigen derives from the microorganism responsible for the disease, for example tuberculin from *Mycobacterium tuberculosis*, typhoidin from *Salmonella typhi*, and abortus from Brucella, and sensitization occurs as a result of a chronic infection. DTH can manifest itself as either focal or systemic. The most characteristic focal manifestation of DTH is a skin reaction exemplified by the tuberculin test. Whole body (systemic) reactions occur particularly in cases in which large quantities of the antigen enter the blood stream. Symptoms of systemic reaction are fever, malaise, backache, pains in the joints, and reduction in the number of circulating lymphocytes. Severe cases of systemic reactions may result in shock, and even death, several hours after the antigen injection.

A rough scenario of the main events in DTH can be outlined as follows. The first exposure of an organism to the antigen results in sensitization of lymphocytes carrying the corresponding receptors on their surfaces. Following the second exposure to the antigen, the same diffuses through the skin and enters small veins. A few sensitized lymphocytes that have reached the site by chance recognize and bind the antigen, and this binding restimulates these cells. The restimulated lymphocytes release MIF. MIF acts on monocytes in the blood making them sticky and the sticky cells then adhere to the endothelial lining of the vein. MIF may also act on the endothelial lining, causing direct damage that may attract more monocytes. The invading monocytes force themselves through the endothelium of the vessel wall and enter the surrounding tissue. There, some of the cells transform morphologically into macrophages while others remain morphologically indistinguishable from blood monocytes. The result is an accumulation of monocytes and monocyte-like cells at the site of injection--the mononuclear cell infiltration. The macroscopic phenomena seen in DTH are swelling of the injection site caused by cellular infiltration, reddening caused by damage to the underlying blood vessels, and necrosis caused by enzymes and factors released by activated monocytes and lymphocytes.

One particularly relevant type of DTH is contact sensitivity, such as dermatitis brought about by inducing agents, including poiston ivy, poison oak, primrose, etc. MIF also plays an ubiquitous role in this type of DTH (see, generally, Klein, J., *Immunology. The Science of Self-Nonself Discrimination*, John Wiley & Sons, 1982, Chapters 7 and 12, at pp. 257–259 and 463–471).

Human MIF has been partially purified and characterized by gel filtration, immunoelectrofocusing (IEF) and sensitivity to proteases and neuraminidase (Weiser, W. Y., et al., *Journal of Immunology*, 126:1958 (1981)). The biochemical heterogeneity of MIF was found to relate to the duration of incubation of the lymphocytes and the antigen used. Klein, supra, indicates (see page 258, Table 7.2) that human MIF has a molecular weight of 25,000 daltons and is stable at 56° C., migrates with human albumin on disc gel electrophoresis, is resistant to neuraminidase, and is sensitive to chymotrypsin. However, the material available prior to the present invention was not homogeneous as defined by strict sodium dodecylsulphate polyacrylamide gel electrophoresis standards, and no process of purifying MIF to such homogeneity was available.

Given the great importance of MIF in delayed type hypersensitivity, the need for a homogeneous standard usable in diagnostic immunology as well as possible therapeutic uses, the purification thereof was clearly a desirable goal.

SUMMARY OF THE INVENTION

The present invention arose out of the discovery of a biochemical purification scheme which allows, for the first time, the preparation of human MIF in homogeneous form. The invention encompasses the human MIF per se as well as natural and equivalent pharmaceutically acceptable salts and pharmaceutically acceptable derivatives.

The invention also concerns compositions, such as diagnostic compositions, containing human MIF and methods of using these in diagnosis.

In other aspects, the invention concerns a process for preparing homogeneous human MIF.

BRIEF DESCRIPTION OF THE PREFERRED EMBODIMENTS

Figure 1:
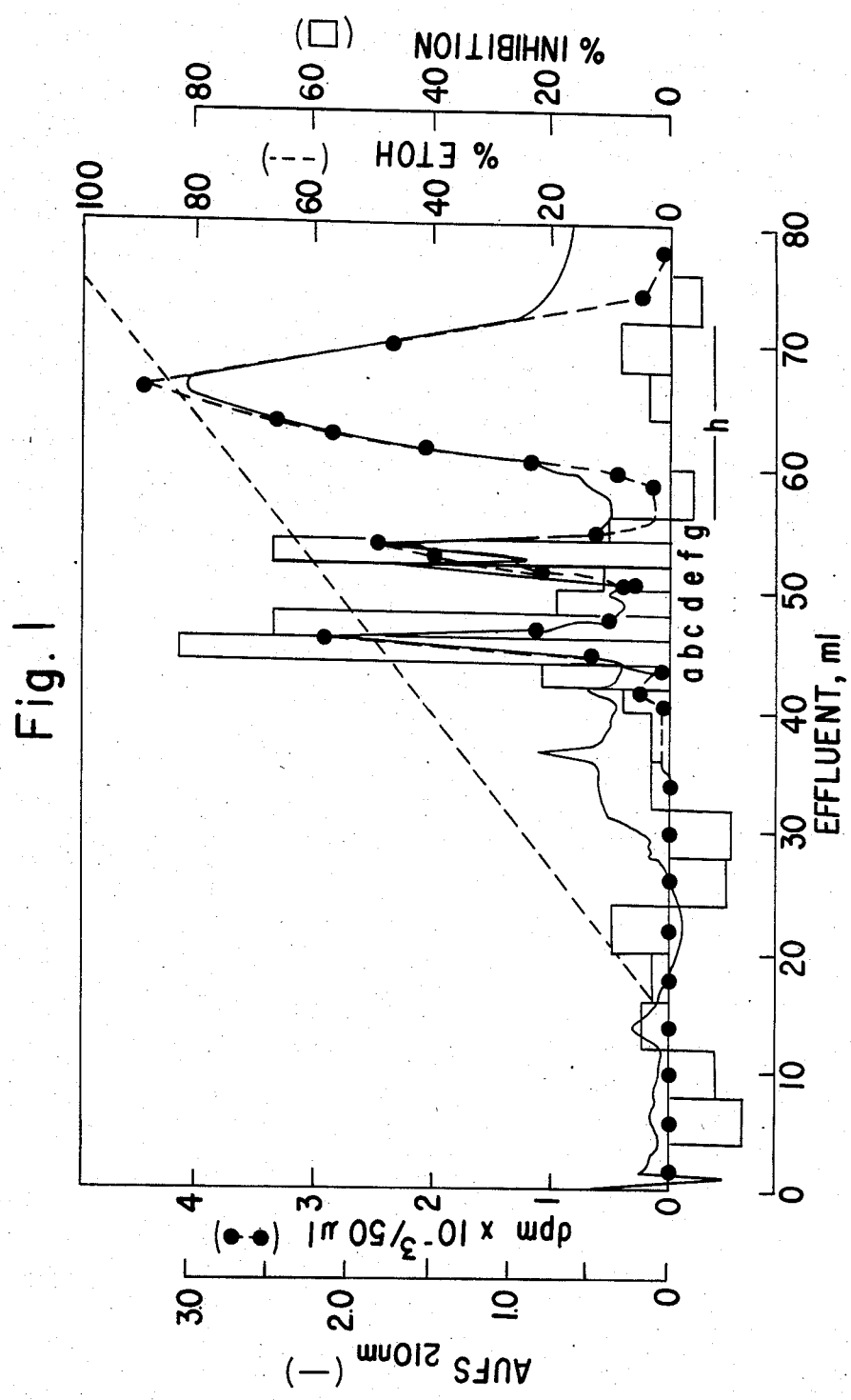
FIG. 1 shows the fractionation of Mo cellderived MIF on reverse phase HPLC (RP-HPLC). The ordinate indicates the radioactivity in 50 microliters of each fraction (-●-●-●-), the extinction at 210 nm (———) in absorbance units at full scale (AUFS), the ethanol gradient (-----), and the percent inhibition of migration of the fractions (■). The pooled active fractions of the second isoelectrofocusing step originating from 1.3 liters of crude conditioned medium (65 mg of protein) were applied to a $C_{18}$ column. 1 ml fractions were collected into tubes containing bovine serum albumin (final concentration 10 mg per ml). Two fractions (2 ml) were pooled, dialyzed, and 30 ml portions of the pooled fractions were assayed for MIF activity. The discrepancy in the radioactivity and the extinction in fractions e+f showing one radioactive peak and two extinction peaks is based on the limited resolution of the radioactive tracing.

The production of MIF by mitogenic stimulation of the cell line Mo, a human T-lymphoblast line derived from a patient with a T-cell variant of hairy-cell leukemia has been previously described (see, for example, Remold, H. G., et al., *Cellular Immunology*, 78:305 (1983)). The Mo cells produce a variety of lymphokines including colony-stimulating factor (CSF) (see Lusis, A. J., et al., *Nature*, 298:75 (1982)) and gamma-interferon (Nathan, I., et al., *Nature*, 292:842 (1981)). The Mo cell line is described in U.S. Pat. No. 4,438,032. The elaboration of large quantities of MIF by Mo cells (10-100 times more than in peripheral blood lymphocytes) provided the opportunity for a large scale biochemical purification of MIF, since these cells can be grown in a large volume.

Briefly, purification of MIF was achieved by the sequential use of gel filtration, hydrophobic affinity chromatography and phenylsepharase, isoelectrofocusing (IEF) and reverse phase high performance liquid chromatography (RP-HPLC).

As used herein the term "salts" refers to both salts of carboxy groups of the polypeptide or protein chain and to acid addition salts of amino groups of the polypeptide chain. Salts of a carboxy group may be formed with either inorganic or organic bases by means known in the art per se. Inorganic salts include, for example, sodium, calcium, ammonium, ferric or zinc salts, and the like. Salts with organic bases include those formed, for example, with amines such as triethanolamine, arginine, or lysine, piperidine, caffeine, procaine and the like. Acid addition salts include, for example, salts with mineral acids such as, for example, hydrochloric acid or sulfuric acid, and salts with organic acids such as, for example, acetic acid or oxalic acid.

Derivatives may also be prepared from the functional groups which occur as side chains on the residues of the N- or C-terminal groups, by means known in the art, and are included in the invention as long as they remain diagnostically acceptable. These derivatives may, for example, include:

aliphatic (e.g. lower ($C_1-C_4$) alkyl) esters of the carboxylic groups;

amides of the carboxylic groups by reaction with ammonia or with lower primary or secondary amines;

N-acyl derivatives which are derivatives of an amino group of the polypeptides formed with acyl moieties (e.g., lower alkanoyl or carboxylic aroyl groups); or O-acyl derivatives which are derivatives of a hydroxy group (for example that of seryl, or threonyl residues) formed with lower acyl moieties.

Both the salts and the derivatives encompassed by the invention are those which are diagnostically acceptable, i.e. those which do not destroy the antigenicity of MIF.

The term "PAGE" is electrophoresis as performed on a polyacrylamide gel and separates proteins or peptides on the basis of charge. If sodium dodecylsulfate (SDS) is incorporated into the gel (SDS-PAGE), the surface active nature of SDS results in a uniform negative charge on the peptide or protein which is a function of size. The result is that separation is based on the molecular size. Native PAGE denotes the employment of this technique without the presence of SDS, and thus proteins are separated on the basis of charge.

Isoelectrofocusing can be performed as a form of native PAGE wherein a pH gradient is maintained across the electrodes, causing each protein to stop, or "focus" at its isoelectric point. However, other supports, preferably for example dextran, typically Ultrodex LKB, are also practical.

Under suitable circumstances, chromatographic procedures may be carried out preferably in a narrow bore column containing a fine particle resin under increased pressure to enhance the effectiveness of separation, i.e., by high pressure liquid chromatography.

Concentration and salt removal are commonly used precursors to certain chromatographic or separation techniques employed in the invention. Salt removal may be performed by, for example, dialysis or gel filtration or by a relatively recently developed technique called control pore glass (CPG) chromatography.

A number of gel filtration and concentration techniques are also used. Certain commercially available materials are especially useful. Pellicon membrane is a sheet-like material composed of Polysulfone manufactured by Millipore, Inc. An Amicon membrane is a similar material also composed of Polysulfone and manufactured by Amicon. These materials are capable of retaining large molecules while permitting passage of smaller ones. They thus operate in the opposite way to molecular sieves, which allow large molecules to pass readily but retard the passage of smaller ones. Both Pellicon and Amicon are useful as concentration tools permitting the smaller molecules to be "filtered" away from the desired macromolecular structures.

Salt removal is generally necessary if ion exchange or other techniques which depend on total ionic strength are employed. These preparation methods and the extent to which they are required for particular separation procedures are well known in the art.

The term "specific activity" refers to the activity of MIF in standard MIF assays as related to the amount of protein by weight in the sample. As specified in the current disclosure, the activity of MIF is measured in terms of "units" which refer to the amount of MIF required to cause 50% inhibition of migration according to either of the assay procedures set forth hereinbelow.

"Impurities" as they pertain to MIF prepared by the method of this invention refers to those substances associated with MIF in its normal cellular environment or in a crude extract, filtrate or centrifuge.

"Homogeneity" is defined as the substantial absence of other proteins of human origin.

Generally, if concanavalin A-stimulated peripheral cells are utilized for the production of MIF, three different forms thereof are seen. One is an early form appearing at six to seven hours which has a molecular weight of about 25,000, an isoelectric point pI of 5.2 and is neuraminidase insensitive. This is probably the form referred to by Klein, supra, at 258. Two later forms are also seen (at about 18 hours) both being glycosylated and neuraminidase sensitive. One has a pI of 5.2 and the other a pI of 3.0, both having a molecular weight of about 32,000-34,000. The MIF purified in the present disclosure from Mo cells has a molecular weight of 32,000-34,000, a pI of 5.2, and is neuraminidase sensitive.

PREFERRED PURIFICATION PROCESS

Production of MIF. For the production of MIF Mo-cells were cultured at $1 \times 10^6$/ml in serum free Iscove's medium in 3% PHA (Burroughs Wellcome) and 5 ng/ml phorbol myristic acetate (TPA) for 96 hours at 37° C. TPA was added 2 hours prior to the addition of PHA. Control supernatants were obtained by incubation of the Mo-cells in the absence of PHA and TPA and reconstitution of PHA and TPA after removal of the cells from the supernatants by centrifugation. After removal of the cells, the media were concentrated by vacuum dialysis to 1/100 of the original volume and stored at −70° C.

A. Sephadex G-100 Gel Filtration

Concentrated crude supernatants were filtered over a Sephadex G-100 column. The void volume (fraction I), effluent containing molecules with an apparent $M_r$ of 95,000-85,000 (fraction II), with an apparent $M_r$ of 85,000-70,000 (fraction III), with an apparent $M_r$ of 70,000-50,000 (fraction IV), with an apparent $M_r$ of 40,000-50,00 (fraction V), and molecules with an apparent $M_r$ of 40,000-25,000 (fraction VI) were pooled and concentrated to 3 ml. The protein content of the fractions was determined by their extinction at 280 nm ($A^{280}$) or by determining the radioactivity of the particular fraction in a beta-counter.

Radiolabeling of MIF

The active fractions obtained from Sephadex G-100 fractionation were radiolabeled by reductive methylation (Jentoff, N., et al., *J. Biol. Chem.*, 254:4359 (1979)). To 5-10 ml of the concentrated, pooled active fractions were added 2 mM $C^{14}$ formaldehyde (40-60 mCi/umol, NEN), 20 mM $NaCNBH_3$ (Aldrich Biochemical Corp.) and 500 mM Hepes buffer, pH 7.5. After an incubation for 2 hours at room temperature, the mixture was passed over a Sephadex$^R$ G-25 column (10×1 cm). The protein was eluted in the void volume of the column and stored frozen in aliquots at −70° C. The specific radioactivity of the active radiolabeled Sephadex G-100 fractions was $1.4 \times 10^4$ dpm/ug protein.

B. Phenylsepharose Affinity Chromatography

The active Sephadex G-100 fractions II and III were pooled, dialyzed against a 20 mM Tris HCl, pH 8.0/20 mM NaCl/5.3 mM $MgClo_4$/0.3 M EDTA buffer (Tris/saline/Mg buffer) made 40% in ammonium sulfate and chromatographed on a phenylsepharose column (10×1 cm, Pharmacia). The column was washed with 30 ml of Tris/saline/Mg buffer/40% ammonium sulfate. A linear gradient consisting of 75 ml of Tris/saline/Mg buffer/40% ammonium sulfate and of 75 ml of Tris/saline/Mg buffer/50% ethylene glycol was used. Twelve fractions were collected. Each fraction was concentrated to 3 ml and 30-40 µl were assayed for MIF activity.

C. Isoelectrofocusing (IEF)

The active fractions from the phenylsepharose step were pooled and dialyzed against $H_2O$ (4 liters for 3 hours, 3 changes) prior to isoelectrofocusing. The fractions were then subjected to isoelectrofocusing in a sucrose density gradient as described in Remold, H., et al., *J. Immunol.*, 118:2015 (1977). Thirteen fractions were collected with a pH-range from 2.0-6.5. The amount of protein in the second IEF step was measured by determining the radioactivity $1.4 \times 10^4$ dpm=1 µg protein. The pooled fractions were dialyzed against Tris/saline/Mg buffer by using dialysis tubing with a cutoff of $M_r$ 12,000 (Fisher Scientific). The fractions were concentrated to 4.0 ml by vacuum dialysis and samples ranging from 0.1-0.2 ml of each fraction were assayed for MIF activity. The remainder was stored at −70° C.

D. Reverse Phase High Performance Liquid Chromatography

The active IEF fractions were dialyzed against 0.04% trifluoroacetic acid (TFA) pH 2.4 and applied to a C-18 column (Waters Assoc.) using a Spectrophysics HPLC system. After the collection of 15 ml effluent, a linear 1-100% ethanol gradient in 0.04% TFA was applied. Twenty-three fractions were collected, dialyzed against Tris/saline/Mg buffer and concentrated to 2 ml. 0.3-0.6 ml were assayed for MIF activity. The remainder was stored at −70° C. The amount of protein present in the fractions was measured by determining the radioactivity in the fractions (vpm=1 µg protein).

E. $NaDodSO_4$/polyacrylamide Gel Electrophoresis

Fractions were prepared for electrophoresis by adding thereto NaDodSO$_4$/2% mercaptoethanol/0.033 M Tris base/0.022 M phosphate, pH 7.0. The method of Laemmli (*Nature*, 227:680 (1970)) was used to separate the polypeptide chains using 10-14% polyacrylamide slab gels. The standard proteins, transferrin, bovine serum albumin, rabbit gamma globulin-heavy chain, ovalbumin, rabbit gamma globulin-light chain, and cytochrome C indicated $M_r$'s of 80,000, 69,000, 52,000, 43,000, 22,000, and 12,000, respectively. The $C^{14}$ labelled polypeptides were visualized by fluorography (Bonner, W. M., et al., *J. Biochem.*, 46:83 (1974)).

F. Assay for MIF

MIF activity was either assayed using the capillary tube macrophage migration inhibition method (David J. R., et al., in *In Vitro Methods of Cell-Mediated Immunity*, Academic Press, NY, p. 249 (1971)) or the agarose microdroplet method (Harrington, J. T., et al., *J. Immunol.*, 110:752 (1973)). In the capillary tube macrophage migration inhibition method, the fractions were diluted to 2 ml with MEM-PS containing 15% guinea pig serum as described. The fractions were placed in duplicate in 1 ml Mackaness chambers together with capillaries containing packed monocytes or guinea pig peritoneal macrophages elicited with mineral oil (Marcol, 52, Exxon Corp., 30 ml per animal i.p. four days prior to assay). Migration of macrophages out of capillaries was measured at 18-22 hours and MIF activity was calculated as percent inhibition of migration of the active fractions relative to that of parallel control fractions containing medium alone. When the agarose microdroplet method was used, 100 $\mu$l of the fractions to be tested were added to flat bottom microtiter wells, each containing one agarose droplet consisting of 105 monocytes suspended in 1 $\mu$l of 0.2% agarose (Seaplaque) in MEM-PS. The microtiter plates were incubated for 20 hours, and the migration of cells out of the droplet was determined by measuring the diameters of the agarose droplet and of the cell migration area. MIF activity was calculated as percent inhibition of migration of the active fraction relative to that of the control fraction. One unit of MIF activity is defined as the amount of MIF which causes 50% inhibition of migration.

Production of Monoclonal Antibody Against MIF

Monoclonal antibodies were raised against MIF purified by Sephadex G-100 gel filtration, phenylsephose affinity chromatography and isoelectrofocusing in BALB/c mice. One hundred $\mu$l of the antibody preparation obtained from the hybrid cell supernatants by precipitation with 45% ammonium sulfate neutralized an amount of MIF yielding 50% inhibition of migration.

Results

Figure 2:
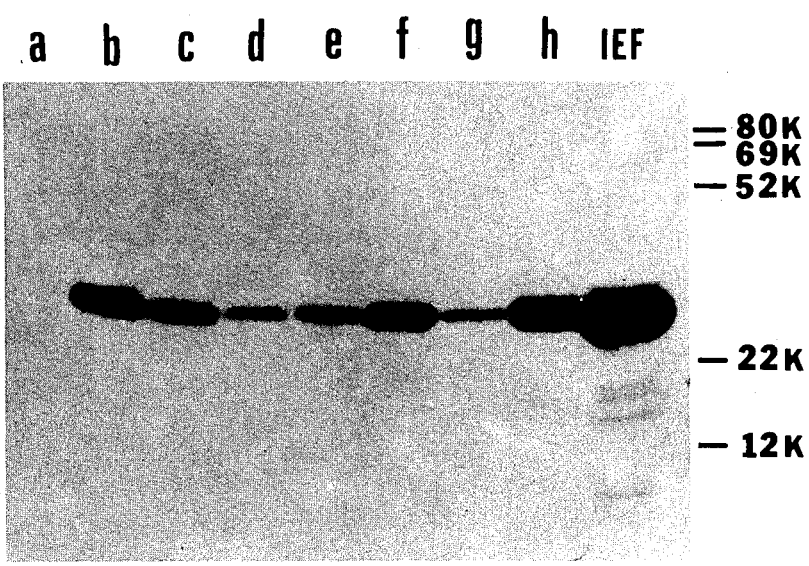
FIG. 2 shows a fluorograph of SDS-PAGE of 50 ml fractions a-b from RP-HPLC (FIG. 4) and 10 ml of the active fraction from the second isoelectrofocusing step. A polypeptide with a $M_r$ of 32,000-34,000 is the only component found in the RP-HPLC step.

FIG. 1 shows the chromatogram of MIF subjected to reverse phase (RP) HPLC on C18 columns. Upon development of the column with ethanol, two species of MIF could be eluted which can be differentiated by their slightly different hydrophobic properties. When these two MIF species were analyzed by SDS-polyacrylamide electrophoresis under reducing conditions, in both cases a single band with an apparent $M_r$ of 32,000-34,000 was detected (FIG. 2). The large protein peak eluting from the RP-HPLC column at a high ethanol concentration which lacks MIF activity (FIG. 1, h) was also analyzed on SDS-polyacrylamide electrophoresis. This material also yielded a band with a $M_r$ of 32,000-34,000. Thus, the different proteins eluted from the C18 column (fractions b+c, f and h in FIG. 1), which elute with increasing ethanol concentrations and of which fractions b+c and f have MIF activity, and can be readily differentiated from each other. They are, however, indistinguishable from each other on gradient (10-14%) SDS-gels.

Figure 3:
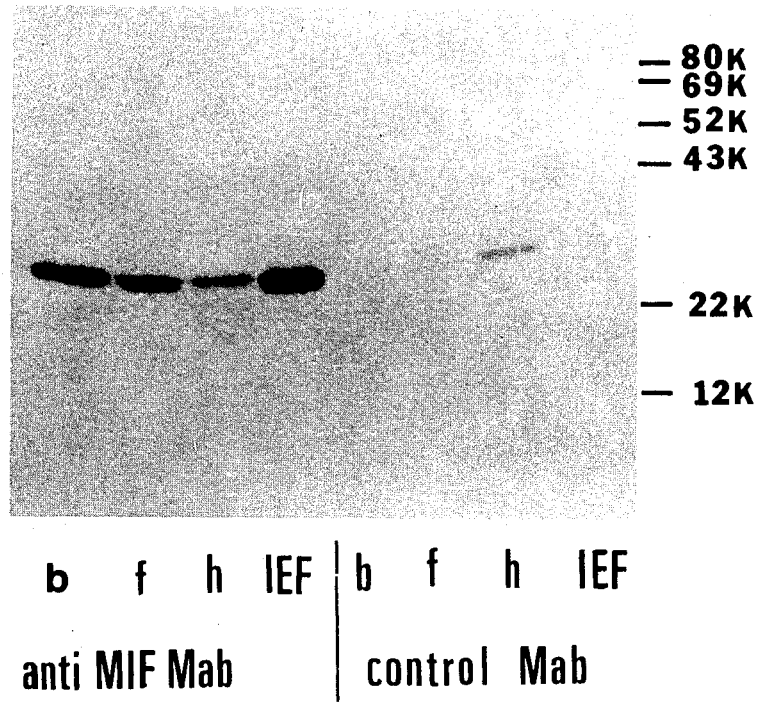
FIG. 3 shows 100 ml of the RP-HPLC fractions b, f, h and a 10 ml aliquot from the active fractions of the second IEF step, incubated with 550 ml anti-MIF- monoclonal antibody (MAB) Sepharose (b1, f1 and IEF1) or immobilized control antibody (b2, f2 and IEF2). The Sepharose gel slurry was washed and the bound proteins were extracted as described. The supernatants were then electrophoresed and fluorographed. Only the immobilized alpha-MIF-Sepharose bound the 32,000 $M_r$ protein and the active fractions d and f (b1 and f1) and in the active fractions from the second isoelectrofocusing step (IEF1). The immobilized control MAB did not bind these substances (b2, f2, IEF2). Alpha-MIF-Sepharose and control MAB both slightly interact with the polypeptide in h, which indicates nonspecific adsorption (h1 and h2).

The fractions b, f and h were incubated with anti-MIF monoclonal antibody (anti-MIF-MAB) and subsequently with protein A-agarose. Analysis of the proteins associated with the anti-MIF-MAB-protein A-agarose by SDS-PAGE showed that the 32,000-34,000 $M_r$ component was specifically interacting with the anti-MIF-MAB (FIG. 3, lanes B1-IEF1), because a nonspecific monoclonal control antibody did not bind these proteins (FIG. 3, lanes b2-IEF2). Protein A Sepharose alone also did not bind these polypeptides (experiments not shown). An exception is fraction h which contains no MIF activity but binds to anti-MIF-MAB and control monoclonal Ab to the same extent. The protein fraction h, therefore, seem to interact nonspecifically with monoclonal antibodies (FIG. 3, lanes h1 and h2). These experiments indicate that the polypeptides in fractions b and f of the RP-HPLC fractionation indeed represent the biologically active material.

Figure 4:
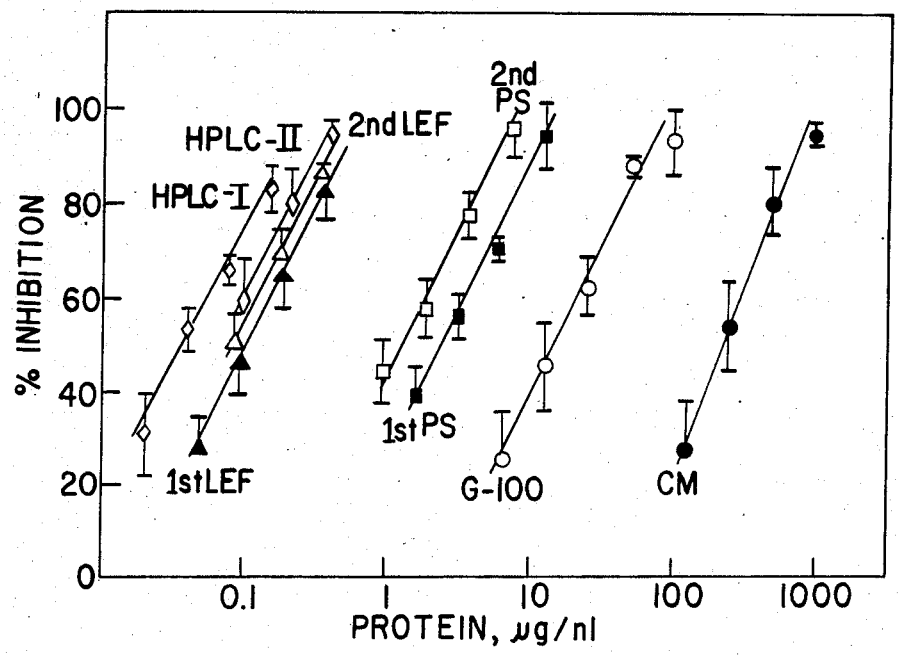
FIG. 4 shows the specific activity of MIF after the different purification steps. The ordinate shows MIF activity and the abscisa the protein concentration of the fractions. Legend: CM: conditioned medium; G-100: Sephadex G-100 gel filtration; PS: phenylsepharase affinity chromatography; IEF: isoelectrofocusing; HPLC-I: fraction b+c from RP-HPLC; HPLC-II: fraction f from RP-HPLC.

The described purification methods, therefore, yield MIF purified to homogeneity. The specific activity of the Mo-MIF at the various stages of purification is demonstrated in FIG. 4 in which the biological activity of a number of dilutions of the different purification steps is plotted against their protein content. When 4 liters of MIF containing conditioned medium were purified by the methods described, two MIF species were obtained with a yield of 5 and 2%. The purification of these two species was 6100-fold and 3200-fold. These data suggest that MIF is a major component of the lymphokines produced by Mo-cells following PHA and TPA stimulation.

Purification of unlabelled MIF by the process of the invention can be carried out by repeating the process as described without radiolabelling the active G-100 fractions. Instead, trace amounts of homogenous labelled MIF can be run in parallel, in order to ascertain the fraction or fractions of unlabelled MIF in the Sephadex, HPLC, Sepharose and IEF procedures.

Physicochemical and Biochemical Characterization of Homogeneous MIF

The protein isolated by the present procedures has a molecular weight of about 32,000-34,000; a pI of about 5.2; one band on SDS-PAGE; a specific activity greater than $1 \times 10^4$ units/mg, preferably greater than $2 \times 10^4$ units/mg. The protein is resistant to neuraminidase treatment; resistant to trypsin treatment, and sensitive to chymotrypsin treatment. It is heat stable at 56° C. for one-half hour; and is not affected by reducing conditions in solution at room temperature.

The protein has migration inhibitory factor activity on guinea pig macrophages, on U937 cells, on PMA-treated HL60 cells, and is somewhat less sensitive on human monocytes.

Interestingly, the protein also has colony stimulating factor (CFS) activity on selected cells, such as human bone marrow cells. It does not have activity on KG-1 cells; no granulocytes are produced, but monocytic cells are obtained; it makes nondifferentiated HL60 cells esterase positive. The CSF activity is ten times more sensitive than the MIF assay.

Several uses are possible for the homogeneous MIF of the invention. For example, it can be used as a standard in diagnostic procedures testing for MIF present in samples of human origin, such as serum, joint fluid, or plasma. It can be labeled as by enzyme or radiolabeling and used as labeled antigen in a competitive immunoassay procedure for the presence of MIF in samples. The appearance of MIF can be used as an indication of DTH reaction against a given antigen by a patient. Measuring the levels of MIF can also assess effectiveness of therapy to determine whether MIF production comes back in patients with no or poor DTH. As such, it can generally be used in diagnostic procedures for DTH. Antibodies raised against the purified MIF, such as the antibodies described in the present application, can be used as antidotes to large scale systemic DTH or, locally, in contact sensitivity reactions.

Techniques for detectable labelling of the homogenous MIF of the invention with a radiolabel, an enzyme label or a fluorescent label are well known to those of skill in the art of protein modification and will not be described further. Reference can be made to Chard, *An Introduction To Radioimmunoassay And Related Techniques,* North-Holland Publishing Co., Amsterdam-NY-Oxford (1978), *The Enzyme-Linked Immunoadsorbent Assay (ELISA)* by Voller, A., et al., Dynatech Europe Borough House, Rue du Pre, Guernsey, Great Britain, and *Radioiodination Techniques, Review* 18, Amersham Corporation, by A. E. Bolton, all herein incorporated by reference.

What is claimed as new and intented to be covered by Letters Patent of the United States is:

1. Purified human migration inhibitory factor (MIF) and diagnostically acceptable salts and derivatives thereof, said MIF and said salts and derivatives thereof having (a) colony stimulating activity and (b) a specific activity greater than $1 \times 10^4$ units/mg.

2. The MIF of claim 1 in detectably labeled form.

3. The detectably labeled MIF of claim 2 wherein said detectable label is a radiolabel.

4. The detectably labeled MIF of claim 2 wherein said detectable label is an enzyme label.

5. The detectably labeled MIF of claim 2 wherein said detectable label is a fluorescent label.

* * * * *